United States Patent
Waller et al.

(10) Patent No.: US 10,317,667 B2
(45) Date of Patent: Jun. 11, 2019

(54) COMPRESSIVE PLENOPTIC MICROSCOPY FOR FUNCTIONAL BRAIN IMAGING

(71) Applicant: THE REGENTS OF THE UNIVERSITY OF CALIFORNIA, Oakland, CA (US)

(72) Inventors: Laura Waller, Berkeley, CA (US); Hillel Adesnik, Kensington, CA (US); Nicolas Pegard, Berkeley, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 231 days.

(21) Appl. No.: 15/199,703

(22) Filed: Jun. 30, 2016

(65) Prior Publication Data
US 2017/0003491 A1    Jan. 5, 2017

Related U.S. Application Data

(60) Provisional application No. 62/188,626, filed on Jul. 4, 2015.

(51) Int. Cl.
*H04N 7/18* (2006.01)
*G02B 21/36* (2006.01)
(Continued)

(52) U.S. Cl.
CPC .......... *G02B 21/367* (2013.01); *A61B 5/0042* (2013.01); *A61B 5/0071* (2013.01);
(Continued)

(58) Field of Classification Search
CPC .................................................. G02B 21/367
(Continued)

(56) References Cited

U.S. PATENT DOCUMENTS 6,026,323 A * 2/2000 Skladnev ............. A61B 5/0084
600/547
6,075,891 A * 6/2000 Burman ............... G06K 9/0063
382/190

(Continued)

OTHER PUBLICATIONS

Pegard, Nicolas et al., "Functional brain imaging at cellular resolution with Compressive Light-Field Microscopy", doi:10.1364/ISA.2015.JTh4A.3, Imaging and Applied Optics 2015, OSA Technical Digest (online) (Optical Society of America, 2015), Imaging Systems and Applications 2015, Arlington, Virginia United States, Jun. 7-11, 2015, ISBN: 978-1-943580-00-2, 3 pages.
(Continued)

*Primary Examiner* — Leron Beck
(74) *Attorney, Agent, or Firm* — O'Banion & Ritchey LLP; John P. O'Banion (57) ABSTRACT

A system and method for quantitative functional neuroimaging through thick brain tissue in live animals. A computational imaging method is disclosed that uses plenoptic image acquisition including a first initialization step that identifies individual neurons by their optical signature and provides a reliable estimate of their position in space and a second stimulation-based image processing step that used acquired calibration data to quickly quantify activity in each identified neuron at video frame-rate.

14 Claims, 7 Drawing Sheets

(51) Int. Cl.
| | | |
|---|---|---|
| *G06T 7/00* | (2017.01) | |
| *A61B 5/00* | (2006.01) | |
| *G02B 27/00* | (2006.01) | |
| *G02B 21/16* | (2006.01) | |
| *G02B 3/00* | (2006.01) | |

(52) U.S. Cl.
CPC ............ *A61B 5/4064* (2013.01); *A61B 5/743* (2013.01); *G02B 27/0075* (2013.01); *G06T 7/0016* (2013.01); *A61B 5/7246* (2013.01); *A61B 2560/0223* (2013.01); *G02B 3/0056* (2013.01); *G02B 21/16* (2013.01); *G02B 21/361* (2013.01); *G06T 2207/10016* (2013.01); *G06T 2207/10052* (2013.01); *G06T 2207/10056* (2013.01); *G06T 2207/30016* (2013.01)

(58) Field of Classification Search
USPC .......................................................... 348/79
See application file for complete search history.

(56) References Cited

U.S. PATENT DOCUMENTS

| | | | | |
|---|---|---|---|---|
| 6,109,270 | A  * | 8/2000 | Mah | A61B 5/7264 128/924 |
| 9,736,402 | B2 * | 8/2017 | De Bruijn | H04N 5/332 |
| 9,939,626 | B2 * | 4/2018 | Rho | G02B 21/361 |
| 2002/0018217 | A1 * | 2/2002 | Weber-Grabau | G01N 21/956 356/601 |
| 2005/0024730 | A1 * | 2/2005 | Aizenberg | G02B 1/041 359/620 |
| 2005/0250091 | A1 * | 11/2005 | Maier | A61B 5/0059 435/4 |
| 2006/0194261 | A1 * | 8/2006 | Kim | G01N 33/5008 435/7.2 |
| 2007/0147673 | A1 * | 6/2007 | Crandall | G02B 21/367 382/128 |
| 2010/0034453 | A1 * | 2/2010 | Lynch | G06T 7/0012 382/133 |
| 2010/0105102 | A1 * | 4/2010 | Hanes | A61B 10/02 435/29 |
| 2012/0081704 | A1 * | 4/2012 | Morrow | G02B 6/32 356/302 |
| 2013/0113927 | A1 * | 5/2013 | De Bruijn | G01B 11/026 348/136 |
| 2014/0243681 | A1 * | 8/2014 | Hielscher | A61B 5/6843 600/473 |
| 2014/0339664 | A1 * | 11/2014 | Rossi | H01L 27/14618 257/432 |
| 2015/0126888 | A1 * | 5/2015 | Patel | A61B 5/087 600/538 |
| 2015/0355449 | A1 * | 12/2015 | Orth | G02B 21/16 348/79 |

OTHER PUBLICATIONS

Keller, P.J. et al."Reconstruction of Zebrafish Early Embryonic Development by Scanned Light Sheet Microscopy" Science, vol. 322, pp. 1065-1069, Nov. 14, 2008.

Berry, M. W. et al. "Algorithms and Applications for Approximate Nonnegative Matrix Factorization", Computational Statistics and Data Analysis, vol. 52, 1pp. 55-173 (2007).

Bègue, A. et al. "Two-photon excitation in scattering media by spatiotemporally shaped beams and their application in optogenetic stimulation", Biomed. Opt. Express, vol. 4, pp. 2869-2879, Nov. 18, 2013.

Broxton, M. et al. "Wave optics theory and 3-D deconvolution for the light field microscope", Optics Express, vol. 21, No. 21, pp. 25418-25439, Oct. 17 2013.

Cohen., Lawrence et al. "Optical Measurement of Membrane Potential", Reviews of Physiology, Biochemistry and Pharmacology, vol. 83, pp. 35-88 (1978).

Cohen, N. et al. "Enhancing the performance of the light field microscope using wavefront coding" Optics Express, vol. 22, No. 20, 24817-24839, Oct. 3, 2014.

Denk, W. et al. "Two-photon laser scanning fluorescence microscopy", Science, vol. 248, No. 4951, pp. 73-76, Apr. 6, 1990.

Logothetis, Nikos K., "What we can do and what we cannot do with fMRI", Nature, vol. 453, pp. 869-878, Jun. 12, 2008.

Chen, T-W. et al. "Ultrasensitive fluorescent proteins for imaging neuronal activity", Nature, vol. 499, pp. 295-300, Jul. 18, 2013.

Prevedel, R. et al. "Simultaneous whole-animal 3D imaging of neuronal activity using light-field microscopy", Nature Methods, vol. 11, No. 7, pp. 727-730, Jul. 2014.

Bouchard, M.B. et al. "Swept confocally-aligned planar excitation (SCAPE) microscopy for high-speed volumetric imaging of behaving organisms", Nature Photonics, vol. 9, pp. 113-119, Jan. 19, 2015.

Frantsuzov, P. et al. "Universal emission intermittency in quantum dots, nanorods and nanowires." Nature Physics, vol. 4, pp. 519-522, Jul. 2008.

Pegard, Nicolas et al., "High-speed 3D brain activity quantification with Compressive Light-Field Microscopy," Optics in the Life Sciences 2015, OSA Technical Digest, PDF Article NW2C.3.pdf, Novel Techniques in Microscopy 2015, Vancouver Canada, Apr. 12-15, 2015, ISBN: 978-1-55752-954-1, 3 pages.

Liu, Hsiou-Yuan et al. "3D imaging in volumetric scattering media using phase-space measurements", Optics Express, vol. 23, No. 11, pp. 14461-14471, May 22, 2015.

Levoy, M. et al. "Light Field Microscopy" Proceedings of SIG-GRAPH 25, pp. 924-934 (2006).

* cited by examiner

COMPRESSIVE PLENOPTIC MICROSCOPY FOR FUNCTIONAL BRAIN IMAGING

CROSS-REFERENCE TO RELATED APPLICATIONS

This application claims priority to, and the benefit of, U.S. provisional patent application Ser. No. 62/188,626 filed on Jul. 4, 2015, incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This description pertains generally to medical imaging, and more particularly to functional brain imaging.

2. Background Discussion

Brain tissue is made of an assembly of interconnected cells called neurons that express activity by means of short electrical pulses called action-potentials. Functional brain imaging designates any device or method that is capable of detecting these pulses, directly or indirectly in order to better understand the architecture and observe the behavior of live neural networks. Primary criteria for evaluating functional brain imaging methods are: a) scale, i.e. the ability to quantify activity in many neurons simultaneously in a large volume; b) high spatial resolution, i.e. the ability to measure activity at the scale of a single neuron; c) high temporal resolution, i.e. the ability to separate individual action-potentials; d) non-invasive acquisition for minimally disturbing cell behavior; and e) accuracy, particularly with ability to operate, even in deep layers of brain tissue, where optical scattering effects are significant.

One example of a non-invasive, commercially available, functional brain activity measuring technique is Functional Magnetic Resonance Imaging (fMRI) adapted to monitor activity in full 3D brains, and preferred for very large brains. However, this method observes blood flow instead of directly targeting neurons, leading to poor spatial and temporal resolution.

Other current techniques take advantage of the recent development of engineered calcium-activated fluorescence proteins (e.g. GCaMP) and voltage sensitive dyes for higher spatial resolution. However, they use mechanical scanning to reduce aberrations caused by optical scattering and offer good spatial resolution at the expense of temporal resolution. For instance, two-photon microscopy relies on a non-linear effect to locally excite fluorescence in a diffraction-limited spot that can be scanned along 3 dimensions. The excitation is obtained with high power laser sources in the infrared domain, which is significantly less scattered by brain tissue. Two-photon microscopy provides high resolution images in 3D, but requires fast controlled mechanical scanning which considerably limits temporal resolution.

Another existing technique is Light-Sheet Microscopy, which uses patterned fluorescence illumination, and one scanning axis to selectively target the excitation light along one specific depth level. It is significantly faster than two-photon methods, but still limited to observing one focal depth level at a time. It requires access to the sample from one or two sides, 90 degrees away form the optical axis of the imaging path. Alternative options with a single microscope objective are possible, at the expense of an additional loss in resolution.

Light field microscopy is a further advancement that uses a micro-lens array in the imaging path of a microscope to capture both position and direction of incoming light on a single frame. Acquisition is followed by a computational ray-tracing inversion, or a de-convolution step to reconstruct a volume image. Volume image reconstruction has been implemented for functional brain imaging but existing techniques are unable to correct for optical scattering. Consequently, volume image reconstruction through thick brain tissue leads to blurred reconstructions and losses of information, and the shape of individual neurons can not be reconstructed accurately.

Accordingly, an object of the present description are functional brain imaging systems and methods that provide accurate, non-invasive quantitative recordings of neural activity, simultaneously in a large volume, with high spatial resolution, and high temporal resolution.

BRIEF SUMMARY

An aspect of the present description is system for quantitative functional neuroimaging through thick brain tissue in live animals, and despite scattering.

The systems and methods disclosed herein use a novel computational method that enables single neuron resolution despite optical scattering, and fast sampling rates. In one embodiment, an optical configuration incorporates a commercial fluorescence microscope along with an add-on plenoptic element (e.g. a micro-lens array), along with an algorithm for digital data processing.

An aspect of the technology of this disclosure is a computational imaging method that takes advantage of plenoptic acquisition to maximize information, but does not attempt to reconstruct a volume image. The effects of optical scattering are preserved throughout the entire data processing sequence. The technology operates in two primary steps. A first initialization step identifies individual neurons by their optical signature and provides a reliable estimate of their position in space. In the second step, a fast quantitative algorithm uses calibration data to quickly quantify activity in each identified neuron at video frame-rate. The technology can be implemented on a light field microscope, as an add-on device by inserting a micro-lens array in the imaging path of a fluorescence microscope, or with a on-a-chip, lens-free imaging apparatus that incorporates the plenoptic element directly onto or within a focal distance away from the optical sensor: a board-level low-noise camera or optical detector array. It is also possible to substitute the micro-lens array for other types of plenoptic encoding phase masks such as engineered diffusers and random surface patterns with proper calibration.

The advantages of the technology of this disclosure include: (a) high spatial resolution at the scale of a single neuron; (b) high temporal resolution, determined by the frame-rate of the video camera (100 Hz demonstrated in our prototype); (c) simultaneous monitoring of multiple neurons (500 neurons successfully detected with our prototype) in large volumes (a 200 micrometer cube); (d) simple optical design (as a standalone device, or as an add-on for fluorescence microscope), with no fine alignment required; (e) efficient processing that enables real time quantification of neural activity during experiments, which allows for possible brain machine interfaces; and (f) good performance, even in heavy optical scattering conditions.

In a preferred embodiment, the imaging method of the present description incorporates a learning step with training data. The technology allows the user to either accept to process data after acquisition is completed, or to initiate a fully automated startup calibration procedure prior to stimulating the subject tissue.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

DETAILED DESCRIPTION

Figure 1:
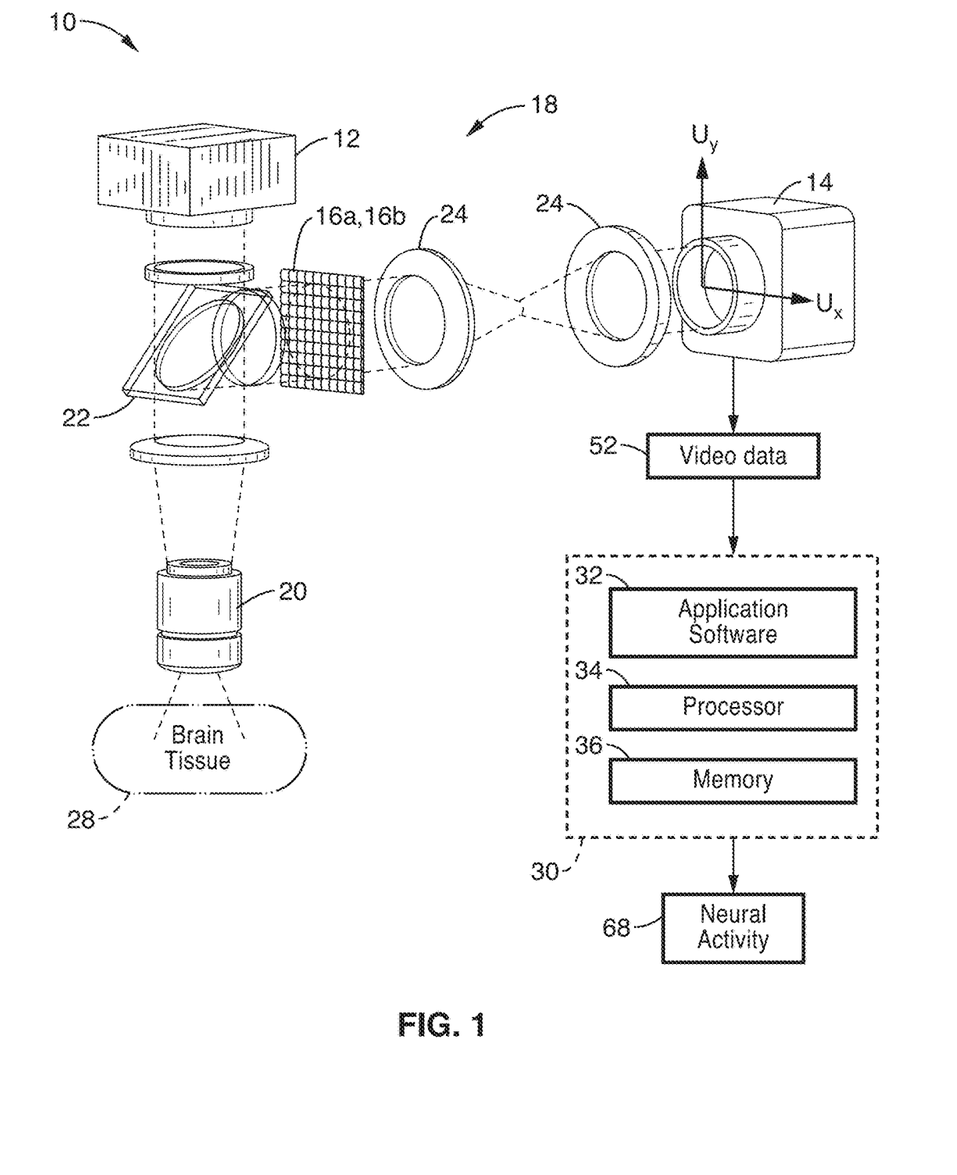
FIG. 1 shows a schematic view of an embodiment of a plenoptic imaging system in accordance with the present description.

FIG. 1 shows a schematic view of an embodiment of a plenoptic imaging system 10 in accordance with the present description. In the embodiment shown in FIG. 1, the system 10 is shown implemented with a fluorescence microscope 18, which may comprise a device specific for use with light field microscopy, or may alternatively comprise a modified fluorescence microscope with an engineered phase mask placed in the imaging plane. It is also appreciated that other devices, such as lens-free fluorescence imager 100 shown in FIG. 10, may also be used in place of microscope 18.

As seen in FIG. 1, an excitation light source 12 (e.g. LED at 488 nm) is directed at brain tissue 28 via intervening optics (e.g. fluorescence filter cube 22 (which may comprise dichroic mirrors/filters) and objective 20. It is to be noted that the brain tissue mass 28 is shown in FIG. 1 in block form; however, the non-invasive methods of the present description are configured to direct light from source 12 into and image the tissue 28 through other anatomy, such as skin, bone, etc.

A plenoptic element 16a, 16b such as a micro-lens array 16a (FIG. 2) or other type of phase mask 16b (FIG. 3) is positioned in the optical path of the image of the tissue, and directed to camera 14 via relay optics 24. In the embodiments of the present description, reconstruction of volume images is not required, and therefore, no fine alignment or calibrations are required. By implementing a plenoptic element 16a, 16b in the imaging path, volume information is acquired by the sensor instead of a 2D projection image.

Figure 2:
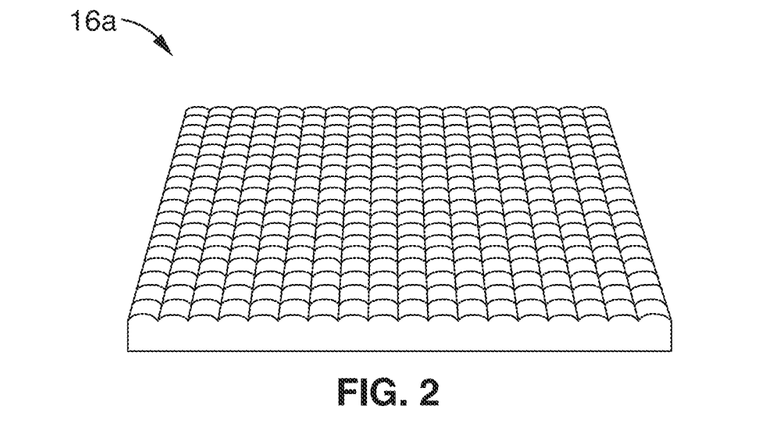
FIG. 2 shows a perspective schematic view of an exemplary micro-lens array configured for use with the imaging system of FIG. 1.

FIG. 2 shows a perspective view of an exemplary micro-lens array 16a. In a typical light-field microscope, the optics generally must be precisely aligned and calibrated (e.g. to the sensor's pixel matrix) to enable accurate volume image reconstruction. However, the non-imaging approach of the present description does not require, and is independent of, actual knowledge of the plenoptic sampling method.

Figure 3:
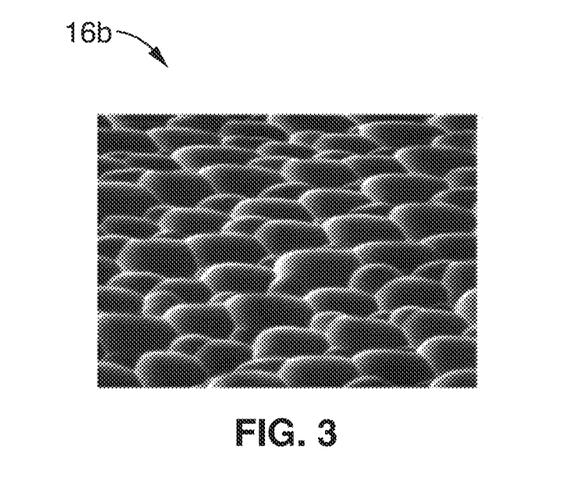
FIG. 3 shows a perspective image of an exemplary phase mask configured for use with the imaging system of FIG. 1.

Furthermore a micro-lens array is not required for system 10, as phase masks are acceptable as long as the spatial pattern allows for efficient sampling of the position and direction of incoming signals. FIG. 3 shows an image of a random phase mask 16b that may be used as the plenoptic element. Alternative plenoptic sampling elements include, but are not limited to, engineered diffusers, artificial phase masks, periodic surface patterns, etc., which may be optimized for the specific type of brain tissue being observed.

Referring back to FIG. 1, video image data 52 from camera 14 is then processed according to computational methods (e.g. method 50 shown in FIG. 4) for performing functional brain imaging to output one or more characteristics of neural activity 68. These processing methods are preferably implemented as instructions within application software 32, which may be stored in memory 36 for execution on processor 34 of computer or server 30.

Figure 4:
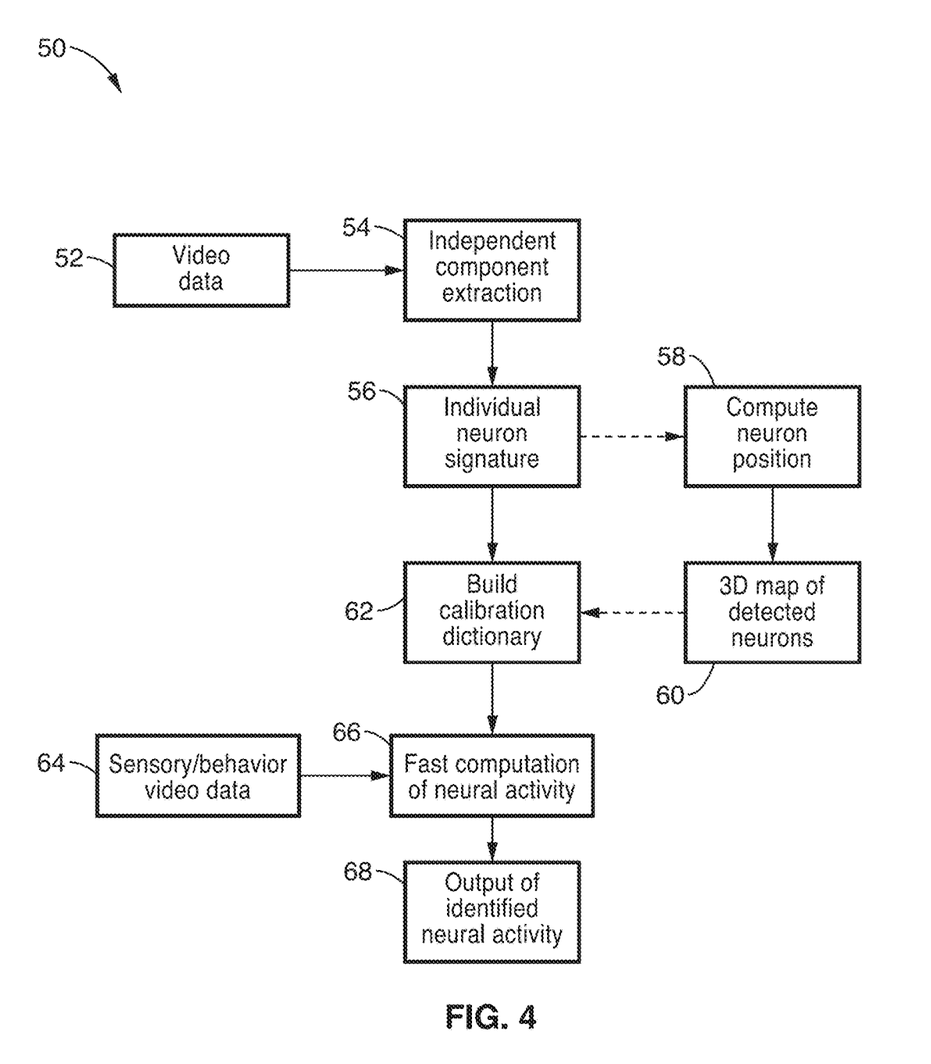
FIG. 4 shows a flow diagram for functional brain imaging method in accordance with the present description.

FIG. 4 shows a flow diagram for functional brain imaging method 50 in accordance with the present description. Functional brain imaging method 50 generally comprises an initialization/calibration phase that builds a calibration dictionary comprising a database of optical signatures (light field signatures) corresponding to the footprint of each identified neuron in the field of view on the camera 14, and a secondary digital processing phase that provides the estimated location in space for each identified neuron. The specific steps for each of these phases are detailed as follows.

Figure 5:
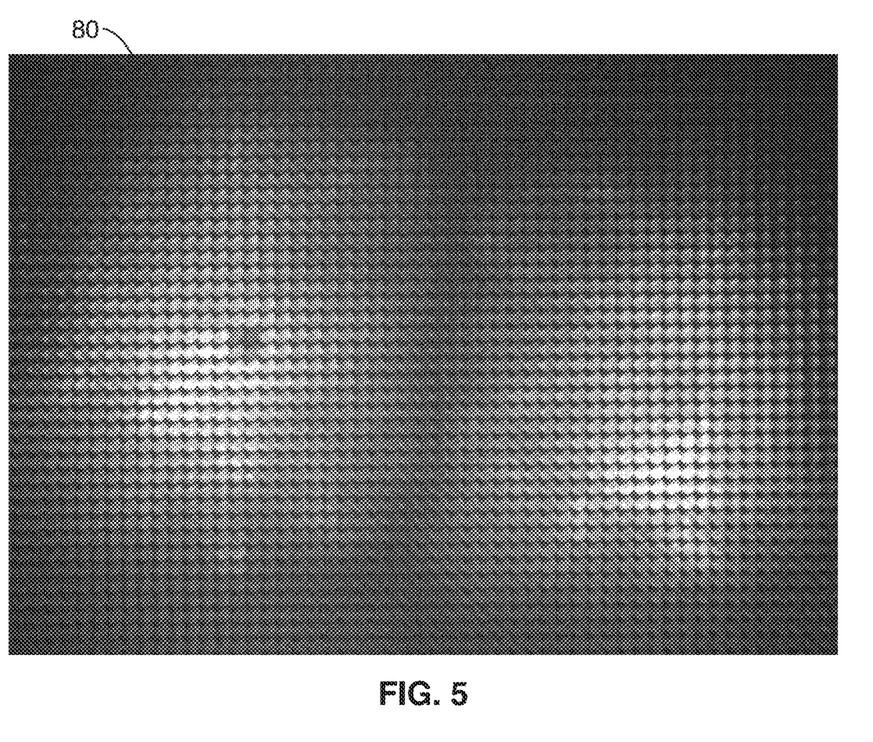
FIG. 5 shows a single still image or frame acquired from a digital camera with a micro-lens array in the optical path

For the initialization phase, initial video data 52 of the excited brain tissue 28 is acquired from the camera 14. The video data generally comprises a length of video with sufficient frames to guarantee that all neurons will have a chance to turn on at some point during the acquisition (background neural activity recording). FIG. 5 shows a single still image or frame 80 acquired with a digital camera (Andor Zyla 5.5 sCMOS) with a micro-lens array 16a in the optical path. After baseline subtraction, the data 52 recorded by the camera 14 represents a 4D sampling of the light-field with position (x,y) and propagation direction ($k_x$; $k_y$) of the fluorescence field over time t, given by I(x, y, $k_x$, $k_y$, t). In the specific case of brain imaging, calcium ions entering the cell through specialized channels change the conformational state of the genetically encoded calcium dye, GCaMP6, so that each neuron's fluorescence correlates tightly to its action potential firing rate. Consequently, the fluorescence light-field I is a linear superposition of all the individual contributions of the Q neurons present in the volume of interest at a given time. We can also assume, in the absence of motion and with good approximation, that for each neuron in the field of view the temporal and spatial properties of fluorescence are independent. Thus, the measurements can be decomposed into a set of independent spatial components that change over time as provide in Eq. 1:

$$I(x, y, k_x, k_y, t) = \sum_{q=1}^{Q} I^{(q)}(x, y, k_x, k_y, t) = \sum_{q=1}^{Q} N^{(q)}(x, y, k_x, k_y) \times T^{(q)}(t) \qquad \text{Eq. 1}$$

where $N^q$ represents the qth spatially independent component, and $T^q$ represents the time-dependent magnitude of each component. In the initialization phase the video camera 14 acquires P frames at constant frame rate dIt. Each frame contains a projection of the light-field I(x, y, $k_x$, $k_y$, t) on a 2D array of M pixels. With the acquired dataset in a M P matrix V=($V_{mp}$), Eq. 1 becomes:

$$V_{m,p} = \sum_{q=1}^{Q} N_{m,q} T_{q,p} \qquad \text{Eq. 2}$$

Figure 6:
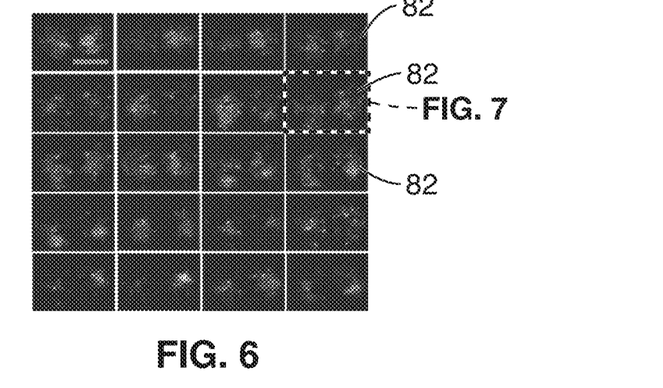
FIG. 6 shows a representation of a series of extracted component images from the image frame of FIG. 5.

If the data is not sparse enough, independent component analysis may be performed at optional step 54 to separate neurons in smaller groups using temporal diversity. FIG. 6 shows a representation of a series of independent, sparse, time-correlated components that are extracted from the video image images 82 from image 80 of FIG. 5. It is noted that The extraction of k independent components in Eq. 2 is achieved by factorization of the raw video data given by: V=NT. This decomposition is akin to compressed sensing, for which many digital methods are available in the art. Here, each neuron's contribution to the fluorescence field is a positive quantity: $V_{mp}$>0; $N_{mq}$>0; and $T_{qp}$>0 and we choose a Nonnegative Matrix Factorization (NMF) algorithm. However, decompression may be performed via one of many types of ICA algorithms available in the art.

The sparsity level in each independent component, N(q), is directly related to the diversity of images in the video acquired during the calibration/initialization step. Because of correlation in neural activity, it is very common to observe multiple neurons always firing simultaneously during the calibration step. This means that this collection of neurons will fall into the same spatial component; however, they may not always activate simultaneously during the digital processing phase, or if a stimulus is presented, causing errors.

At step 56, a secondary decomposition step is performed that operates on each independent component 82 to separate and locate each neuron in 3D, thereby generating an individual neuron signature representing the source and identification for each neuron is generated. Since each has a different spatial location in 3D, its position information is contained in the light field data, but obscured by scattering effects. Sparsity-based optimization may be implemented to accurately localize point sources (such as fluorophores) through thick scattering media, provided there are a sparse number of sources. The initial component extraction step 54 (e.g. using NMF) generally provides that each component contains the signature of only a few neurons. We implement this method for each component in order to distinguish the sparse set of correlated neurons based on their light field signature. Each point source traces out a 2D hyper plane within the 4D light field space. The zero-angle intercepts of the plane define the fluorophore's lateral position, the tilt of the plane defines its depth and scattering serves to spread the light field information in the angle dimension, with deeper fluorophores being both more tilted and having more scattering. Using this model and a sparsity assumption as a priori constraints on the optimization, we are able to successfully separate the component light field into its constituent neurons, extracting their light field signatures.

Figure 7:
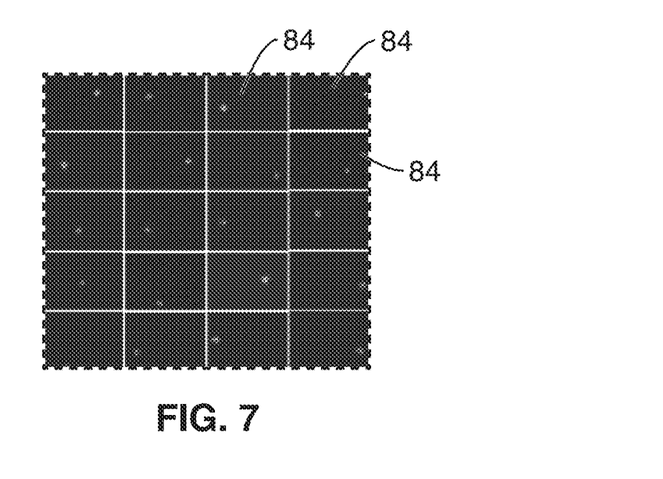
FIG. 7 shows a representation of a series independent neuron images within an independent component image of FIG. 6.

Step 56 essentially splits the sparse or sparsified data into a larger number of frames, that each represent one and only one neuron FIG. 7 shows a representation of a series of independent neuron images 84 within an independent component image 82, wherein each neuron image 84 represents how that individual neuron would look like to the camera 14 if only that neuron were firing or active (e.g. if we were able to silence all neurons in the brain and only turn on the singular neuron). The neuron image 84 is referred to as the "light field signature," and it takes into account all the optical scattering effects affecting light propagation.

Figure 8:
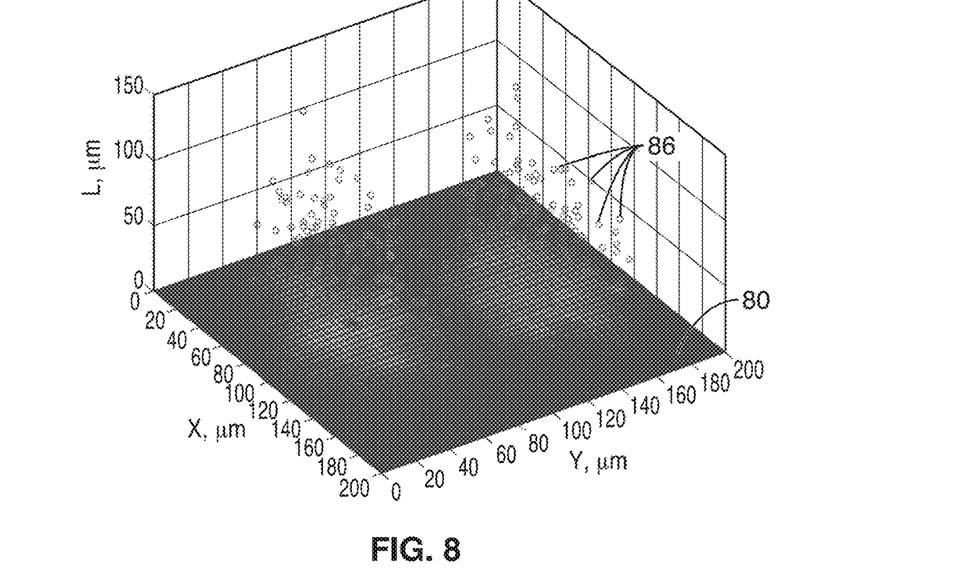
FIG. 8 shows an exemplary 3D map, showing estimated individual neuron locations within a 200 nm cube volume with respect to original image frame.

The individual neuron signatures 84, as acquired in step 56 and shown in an exemplary fashion in FIG. 7, may then be used to directly compile the calibration dictionary at step 62, which contains neuron signature for each component of every frame 80 generated within the video data 52. In an alternative embodiment, the position for each neuron may be computed at step 58 to generate a 3D map of the detected neurons. FIG. 8 shows an exemplary 3D map, showing estimated individual neuron locations within a 200 nm cube volume with respect to original image frame 80. This may be useful to allow display of how neural activity is spatially distributed in space.

Once the initialization/calibration phase is completed, measurement of activity in each neuron is possible, and quantitative measurement of fluorescence in each neuron is retrieved by quickly decomposing any subsequent frame as a linear combination of dictionary elements.

During the second phase, the sample tissue 28 may be subject to various external stimuli to acquire video of sensory/behavior data frames 64. Each frame of the video is decomposed as a linear positive sum of elements of the dictionary. The coefficients of that decomposition indicate directly, which neurons are on, and which are off, at the moment when the frame was taken. At step 66, the neural activity is computed and quickly decomposed as an optimal, positive, linear combination of the dictionary frames from calibration dictionary step 62. The distribution of light among all identified components may be output at step 68, which is a quantitative measure of fluorescence levels in individual neurons indicative of neural activity in all previously identified neurons. In a preferred embodiment, the output data 68 comprises a 2D matrix that shows how neural activity evolves as a function of time for each neuron previously identified (see FIG. 9). The user can also localize each neuron of interest in space by finding the corresponding neuron in FIG. 8.

Figure 9:
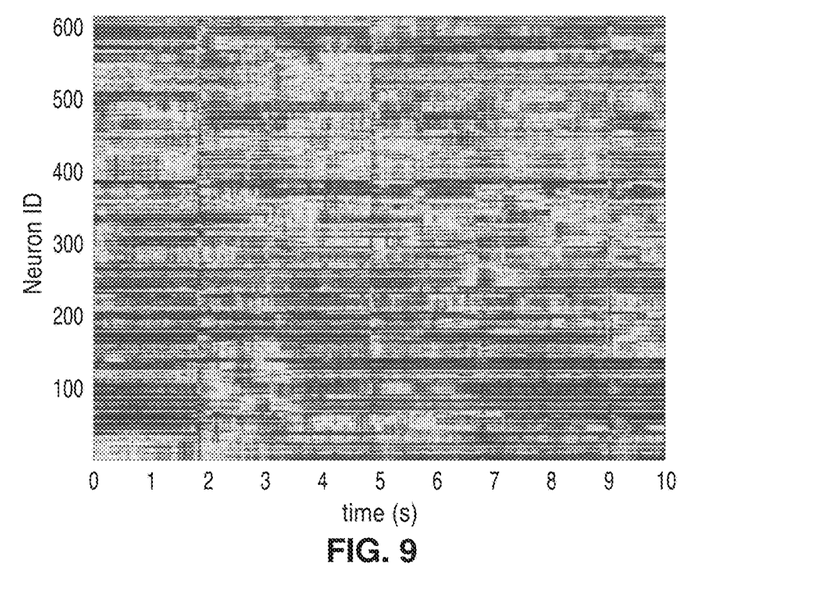
FIG. 9 shows an image of an exemplary fluorescence output of experimental results in live zebra fish showing 600+ identified neurons and quantitative measurement of activity.

FIG. 9 shows an image of an exemplary fluorescence output 68 of experimental results in live zebra fish showing 600+ identified neurons and quantitative measurement of activity, sampled at 50 Hz. In this experiment, a zebra fish was placed in the light field microscope and 50 independent components were extracted from 500 diverse frames captured in the calibration/initialization phase. Each independent component was then further divided into single neuron signatures. The computation of the calibration dictionary yielded a set of 620 light field signatures. 10 seconds of spontaneous brain activity was then recorded at 100 fps, and each farm within the video was decomposed as a linear combination of elements from the dictionary.

Figure 10:
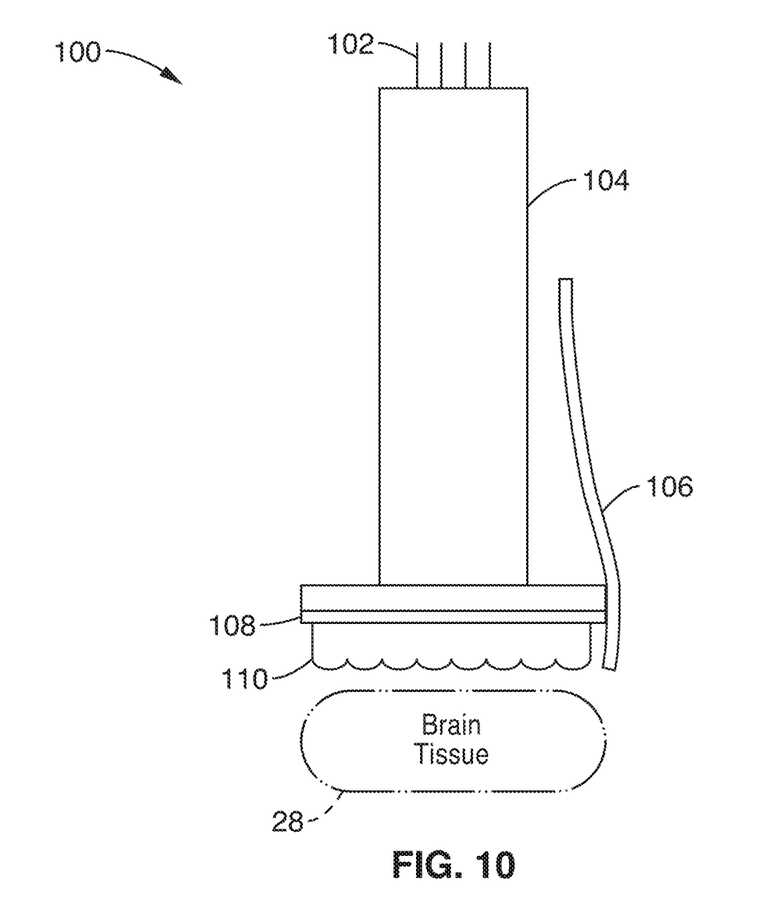
FIG. 10 illustrates a miniaturized, on-a-chip, lens-free imaging apparatus that incorporates the plenoptic element in accordance with the present description.

FIG. 10 illustrates a miniaturized, on-a-chip, lens-free imaging apparatus 100 that incorporates the plenoptic element 110 (e.g. micro-lens array 16a or optical encoding element of phase mask 16b) directly onto or within a focal distance away from the sensor the board-level low-noise camera or optical sensor (CMOS/CCD) 104. The assembled device can be placed directly above the prepared subject for imaging tissue 28. For fluorescence imaging, a spectral emission filter 108 matching the properties of the fluorescence marker to be observed is implemented just above the sensor's surface. An optical fiber or other excitation source 106 may be positioned adjacent the sensor 104 to provide fluorescence excitation light to the tissue 28. In a preferred embodiment, the assembly is kept sealed and aligned with opaque epoxy.

The camera 104 may be wired (e.g. via USB interface), or otherwise coupled in communication with a computer 30 for data acquisition and processing, (i.e. the imaging apparatus 100 may be used in place of microscope 18 in imaging system 10 of FIG. 1). This implementation allows for long lasting, repeated experiments without restraining the subject's head on a fixed stage.

The setup disclosed in FIG. 1 generally requires a steady optical path from brain to sensor, and thus do not allow for motion artifacts at this point. This issue is currently addressed by restraining the sample on a fixed stage, or by using an on-a-chip lens-free device as shown in FIG. 10, that is attached directly to the subject. In addition, computational methods, and motion correction optical techniques may also be implemented.

The technology disclosed herein has been successfully tested for use with engineered proteins such as GCaMP6s, and GCaMP6f for functional brain imaging. Fluorescence is related to the increased concentration of calcium ions in the cytoplasm of active neurons. The technology is compatible with other types of functional optical markers, for instance: voltage sensitive dyes as well as with fluorescence intermittency in quantum dots. Finally, while the present description is primarily directed to functional brain imaging, it is appreciated that the technology is compatible with functional imaging in other tissues or structures that have scattering properties, and is not limited to brain tissue or neuroscience research.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A functional imaging apparatus comprising: (a) a computer processor; and (b) a memory storing instructions executable by the computer processor; (c) said instructions, when executed by the computer processor, performing steps comprising: (i) acquiring initial image data from a sample tissue, the initial image data comprising features corresponding to a plurality of neurons within the sample tissue; (ii) generating a database of individual optical signatures, each of the individual optical signatures corresponding to an identified neuron within the plurality of neurons; (iii) acquiring secondary image data from the sample tissue, the secondary image data comprising features corresponding to a plurality of neurons responsive to an external stimulus applied to the sample tissue; and (iv) decomposing the secondary image data as a function of the database of individual optical signatures to output a quantitative measure of fluorescence levels of the identified individual neurons.

2. The apparatus of any preceding embodiment, wherein the database comprises data corresponding to an estimated location in space for each identified neuron within the plurality of neurons.

3. The apparatus of any preceding embodiment, wherein the secondary image data is decomposed as a function of a positive, linear combination of one or more image frames within database of individual optical signatures.

4. The apparatus of any preceding embodiment: wherein acquiring initial image data comprises acquiring video data from the sample tissue; the video data comprising a plurality of frames; wherein each frame within the video data is decomposed to extract independent sparse, time-correlated components; and wherein the time-correlated components are further decomposed to generate an individual neuron signature representing a source and identification for each neuron within the plurality of neurons.

5. The apparatus of any preceding embodiment, wherein said instructions, when executed by the computer processor, generate a 3D map of detected neurons and their corresponding locations.

6. The apparatus of any preceding embodiment, wherein the quantitative measure of fluorescence levels in individual neurons corresponds to a distribution of light among all identified components within the video data.

7. The apparatus of any preceding embodiment: wherein the initial image data is acquired via a plenoptic element disposed within an image path of the sample tissue; and wherein the plenoptic element has a spatial pattern configured to disperse light within the optical path for sampling of a position and direction of incoming signals corresponding to said light.

8. A method for performing functional imaging, comprising: acquiring initial image data from a sample tissue, the initial image data comprising features corresponding to a plurality of neurons within the sample tissue; generating a database of individual optical signatures, each of the individual optical signatures corresponding to an identified neuron within the plurality of neurons; acquiring secondary image data from the sample tissue, the secondary image data comprising features corresponding to a plurality of neurons responsive to an external stimulus applied to the sample tissue; and decomposing the secondary image data as a function of the database of individual optical signatures to output a quantitative measure of fluorescence levels of the identified individual neurons.

9. The method of any preceding embodiment, wherein the database comprises data corresponding to an estimated location in space for each identified neuron within the plurality of neurons.

10. The method of any preceding embodiment, wherein the secondary image data is decomposed as a function of a positive, linear combination of one or more image frames within database of individual optical signatures.

11. The method of any preceding embodiment: wherein acquiring initial image data comprises acquiring video data from the sample tissue; the video data comprising a plurality of frames; wherein each frame within the video data is decomposed to extract independent sparse, time-correlated components; and wherein the time-correlated components are further decomposed to generate an individual neuron signature representing a source and identification for each neuron within the plurality of neurons.

12. The method of any preceding embodiment, further comprising generating a 3D map of detected neurons and their corresponding locations.

13. The method of any preceding embodiment, wherein the quantitative measure of fluorescence levels in individual neurons corresponds to a distribution of light among all identified components within the video data.

14. The method of any preceding embodiment: wherein the initial image data is acquired via a plenoptic element disposed within an image path of the sample tissue; and wherein the plenoptic element has a spatial pattern configured to disperse light within the optical path for sampling of a position and direction of incoming signals corresponding to said light.

15. A miniaturized, on-a-chip, lens-free imaging apparatus, comprising: a board-level low-noise camera comprising an optical sensor; a plenoptic element disposed directly onto or within a focal distance away from the optical sensor; a spectral emission filter disposed within the optical path of the optical sensor, the spectral emission filter matching properties of a fluorescence marker to be observed within a target tissue; an excitation source positioned adjacent the optical sensor to provide fluorescence excitation light into the target tissue; wherein the apparatus is configured to be placed directly above the prepared subject for the target imaging tissue.

16. The apparatus of any preceding embodiment, wherein the plenoptic element comprises a micro-lens array.

17. The apparatus of any preceding embodiment, wherein the plenoptic element comprises an optical encoding element or phase mask.

18. The apparatus of any preceding embodiment, further comprising: (a) a computer processor; and (b) a memory storing instructions executable by the computer processor; (c) said instructions, when executed by the computer processor, performing steps comprising: (i) acquiring video data of the target tissue and generating compute a dictionary of optical signatures corresponding to each identified neuron in the field of view of the optical sensor; and (ii) acquiring video data of the target tissue in response to an external stimulus and calculating estimated location in space for each identified neuron.

19. The apparatus of any preceding embodiment, wherein as the target tissue is subject to the external stimulus, new data frames are acquired and decomposed as a linear combination of dictionary frames.

20. The apparatus of any preceding embodiment, wherein a distribution of light among all identified components is a quantitative measure of fluorescence levels in individual neurons.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A functional imaging apparatus, comprising:
   (a) a computer processor; and
   (b) a memory storing instructions executable by the computer processor;
   (c) said instructions, when executed by the computer processor, performing steps comprising:
      (i) acquiring initial image data from a sample tissue, the initial image data comprising features corresponding to a plurality of neurons within the sample tissue;
      (ii) generating a database of individual optical signatures, each of the individual optical signatures corresponding to an identified neuron within the plurality of neurons;
      (iii) acquiring secondary image data from the sample tissue, the secondary image data comprising features corresponding to a plurality of neurons responsive to an external stimulus applied to the sample tissue; and
      (iv) decomposing the secondary image data as a function of the database of individual optical signatures to output a quantitative measure of fluorescence levels of the identified individual neurons;
      (v) wherein acquiring initial image data comprises acquiring video data from the sample tissue, the video data comprising a plurality of frames;
      (vi) wherein each frame within the video data is decomposed to extract independent sparse, time-correlated components; and
      (vii) wherein the time-correlated components are further decomposed to generate an individual neuron signature representing a source and identification for each neuron within the plurality of neurons.

2. The apparatus of claim 1, wherein the database comprises data corresponding to an estimated location in space for each identified neuron within the plurality of neurons.

3. The apparatus of claim 1, wherein the secondary image data is decomposed as a function of a positive, linear combination of one or more image frames within database of individual optical signatures.

4. The apparatus of claim 1, wherein said instructions, when executed by the computer processor, generate a 3D map of detected neurons and their corresponding locations.

5. The apparatus of claim 1, wherein the quantitative measure of fluorescence levels in individual neurons corresponds to a distribution of light among all identified components within the video data.

6. The apparatus of claim 1:
   wherein the initial image data is acquired via a plenoptic element disposed within an image path of the sample tissue; and
   wherein the plenoptic element has a spatial pattern configured to disperse light within the optical path for sampling of a position and direction of incoming signals corresponding to said light.

7. A method for performing functional imaging, comprising:
   acquiring initial image data from a sample tissue, the initial image data comprising features corresponding to a plurality of neurons within the sample tissue;
   generating a database of individual optical signatures, each of the individual optical signatures corresponding to an identified neuron within the plurality of neurons;
   acquiring secondary image data from the sample tissue, the secondary image data comprising features corresponding to a plurality of neurons responsive to an external stimulus applied to the sample tissue; and
   decomposing the secondary image data as a function of the database of individual optical signatures to output a quantitative measure of fluorescence levels of the identified individual neurons;
   wherein acquiring initial image data comprises acquiring video data from the sample tissue, the video data comprising a plurality of frames;
   wherein each frame within the video data is decomposed to extract independent sparse, time-correlated components; and
   wherein the time-correlated components are further decomposed to generate an individual neuron signature representing a source and identification for each neuron within the plurality of neurons.

8. The method of claim 7, wherein the database comprises data corresponding to an estimated location in space for each identified neuron within the plurality of neurons.

9. The method of claim 7, wherein the secondary image data is decomposed as a function of a positive, linear combination of one or more image frames within database of individual optical signatures.

10. The method of claim 7, further comprising generating a 3D map of detected neurons and their corresponding locations.

11. The method of claim 7, wherein the quantitative measure of fluorescence levels in individual neurons corresponds to a distribution of light among all identified components within the video data.

12. The method of claim 7:
    wherein the initial image data is acquired via a plenoptic element disposed within an image path of the sample tissue; and
    wherein the plenoptic element has a spatial pattern configured to disperse light within the optical path for sampling of a position and direction of incoming signals corresponding to said light.

13. A functional imaging apparatus, comprising:
    (a) a computer processor; and
    (b) a memory storing instructions executable by the computer processor;
    (c) said instructions, when executed by the computer processor, performing steps comprising:
       (i) acquiring initial image data from a sample tissue, the initial image data comprising features corresponding to a plurality of neurons within the sample tissue;

(ii) generating a database of individual optical signatures, each of the individual optical signatures corresponding to an identified neuron within the plurality of neurons;

(iii) acquiring secondary image data from the sample tissue, the secondary image data comprising features corresponding to a plurality of neurons responsive to an external stimulus applied to the sample tissue; and (iv) decomposing the secondary image data as a function of the database of individual optical signatures to output a quantitative measure of fluorescence levels of the identified individual neurons;

(v) wherein acquiring initial image data comprises acquiring video data from the sample tissue; the video data comprising a plurality of frames;

(vi) wherein each frame within the video data is decomposed to extract independent sparse, time-correlated components; and (vii) wherein the time-correlated components are further decomposed to generate an individual neuron signature representing a source and identification for each neuron within the plurality of neurons.

14. A method for performing functional imaging, comprising:

acquiring initial image data from a sample tissue, the initial image data comprising features corresponding to a plurality of neurons within the sample tissue;

generating a database of individual optical signatures, each of the individual optical signatures corresponding to an identified neuron within the plurality of neurons;

acquiring secondary image data from the sample tissue, the secondary image data comprising features corresponding to a plurality of neurons responsive to an external stimulus applied to the sample tissue; and decomposing the secondary image data as a function of the database of individual optical signatures to output a quantitative measure of fluorescence levels of the identified individual neurons;

wherein acquiring initial image data comprises acquiring video data from the sample tissue; the video data comprising a plurality of frames;

wherein each frame within the video data is decomposed to extract independent sparse, time-correlated components; and wherein the time-correlated components are further decomposed to generate an individual neuron signature representing a source and identification for each neuron within the plurality of neurons.

* * * * *